United States Patent
Panin

(10) Patent No.: US 10,482,596 B2
(45) Date of Patent: Nov. 19, 2019

(54) NORMALIZATION CRYSTAL EFFICIENCIES ESTIMATION FOR CONTINUOUS MOTION BED ACQUISITION

(71) Applicant: Siemens Medical Solutions USA, Inc., Malvern, PA (US)

(72) Inventor: Vladimir Y. Panin, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 272 days.

(21) Appl. No.: 15/586,485

(22) Filed: May 4, 2017

(65) Prior Publication Data

US 2018/0322626 A1 Nov. 8, 2018

(51) Int. Cl.
*G06T 7/00* (2017.01)
*G01T 1/29* (2006.01)
*A61B 6/03* (2006.01)
*A61B 6/04* (2006.01)
*G01T 1/202* (2006.01)

(52) U.S. Cl.
CPC ............ *G06T 7/0012* (2013.01); *A61B 6/037* (2013.01); *A61B 6/0407* (2013.01); *G01T 1/202* (2013.01); *G01T 1/2985* (2013.01); *G06T 2207/10104* (2013.01)

(58) Field of Classification Search
CPC .............................. A61B 6/037; G01T 1/2985
USPC ........................................................ 250/362
See application file for complete search history.

(56) References Cited

U.S. PATENT DOCUMENTS

| 9,044,153 | B2 | 6/2015 | Panin |
| 2014/0200848 | A1 | 7/2014 | Panin et al. |
| 2015/0199302 | A1 | 7/2015 | Qi et al. |
| 2015/0297168 | A1 | 10/2015 | Panin |
| 2017/0091963 | A1 | 3/2017 | Panin |

OTHER PUBLICATIONS

Casey, M. E., et al., "A Component Based Method for Normalization in Volume PET," In Proc. 3rd Int. Meeting on fully three-dimensional image reconstruction in radiology and nuclear medicine, France: Aix-les-Bains, 1995, pp. 66-71.
Defrise, A. et al., "A normalization technique for 3D PET Data," phys. Med. Biol., 1991, vol. 36., No. 7, pp. 939-952.
Casey, M. E., et al., "Quantitation in Positron Emission Computed Tomography: 7. A Technique to Reduce Noise in Accidental Coincidence Measurements and Coincidence Efficiency Calibration," Journal of Computer Assisted Tomography, Sep./Oct. 1986, 10(5):845-850.
Hogg, D., et al., "Maximum-Likelihood Estimation of Normalisation Factors for PET," 2001 IEEE Nuclear Science Symposium Conference Record—vol. 4, (Nov. 2001) pp. 2065-2069.
Bai, B. et al., "Model-based normalization for iterative 3D PET image reconstruction," Phys. Med. Biol. 47 (2002) pp. 2773-2784.
Panin, V. "Monotonic Iterative Algorithms for Crystal Efficiencies Estimation from Normalization Data and Single Rates Estimation from Compressed Random Coincidence Data," IEEE Nuclear Science Symposium and Medical Imaging Conference (2013 NSS/MIC), 2013, pp. 1-6, DOI: 10.1109/NSSMIC.2013.6829375.

(Continued)

*Primary Examiner* — David P Porta
*Assistant Examiner* — Abra S Fein

(57) ABSTRACT

A method and system for simultaneously monitoring a positron emission tomography scanner performance during a continuous-bed-motion acquisition is disclosed.

18 Claims, 9 Drawing Sheets

(56) References Cited

OTHER PUBLICATIONS

Badawi, R.D. and Marsden, P.K., "Self-normalization of emission data in 3D PET," IEEE Transactions on Nuclear Science, vol. 46, No. 3, Jun. 1999, pp. 709-712.
Ishikawa, Akihiro et al., "Self Normalization for Continuous 3D Whole Body Emission Data in 3D PET," IEEE Symposium Conference Record Nuclear Science 2004, vol. 6, pp. 3634-3637, DOI: 10.1109/NSSMIC.2004.1466670.
Belzunce, Martin A. and Reader, Andrew J., "Self-Normalization of 3D PET Data by Estimating Scan-Dependent Effective Crystal Efficiencies," 2015 IEEE Nuclear Science Symposium and Medical Imaging Conference (NSS/MIC), 2015, pp. 1-3, DOI: 10.1109/NSSMIC.2015.7582049.
Salomon, A. et al., "A Self-Normalization Reconstruction Technique for PET Scans Using the Positron Em2240ission Data," IEEE Transactions on Medical Imaging, vol. 31, No. 12, Dec. 2012, pp. 2234.
Panin, V.Y. "Simultaneous Activity and Crystal Efficiencies Reconstruction: TOF Patient-Based Detector Quality Control," 2014 IEEE Nuclear Science Symposium and Medical Imaging Conference (NSS/MIC), 2014, pp. 1-5, DOI: 10.1109/NSSMIC.2014.7430912.
Defrise, M. et al., "Time-of-flight PET data determine the attenuation sinogram up to a constant." 2012 Institute of Physics and Engineering in Medicine, Physics in Medicine and Biology, vol. 57, No. 4, Jan. 31, 2012, pp. 1-18.
Rezaei, Ahmadreza et al., "ML-Reconstruction for TOF-PET With Simultaneous Estimation of the Attenuation Factors," IEEE Transactions on Medical Imaging, vol. 33, No. 7, Jul. 2014, pp. 1563-1572.
Panin, V.Y. et al., "Continuous bed motion on clinical scanner: design, data correction, and reconstruction," Phys. Med. Biol. 59 (2014) 6153-6174.
Search Report for Corresponding European Application No. 18170350, dated Sep. 25, 2018.

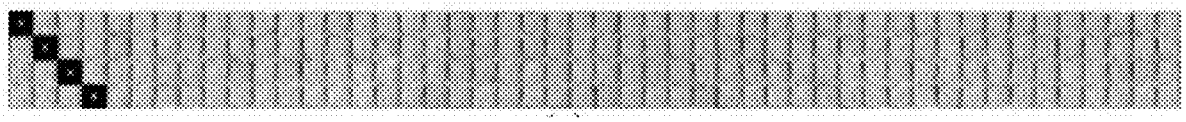
FIG. 8A
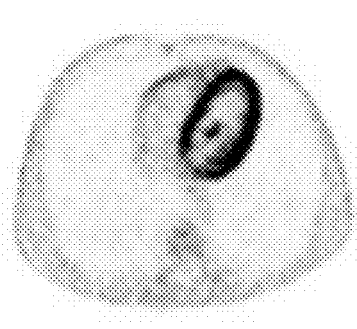
FIG. 8B
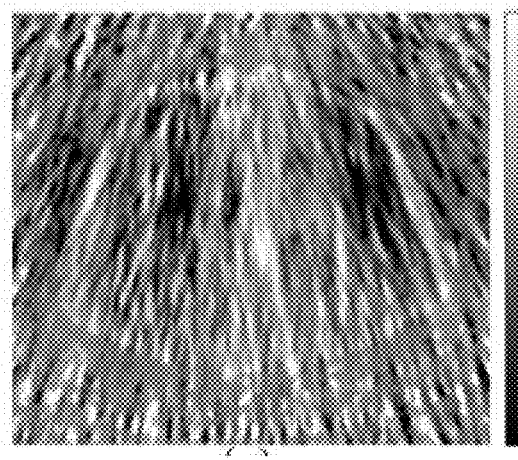       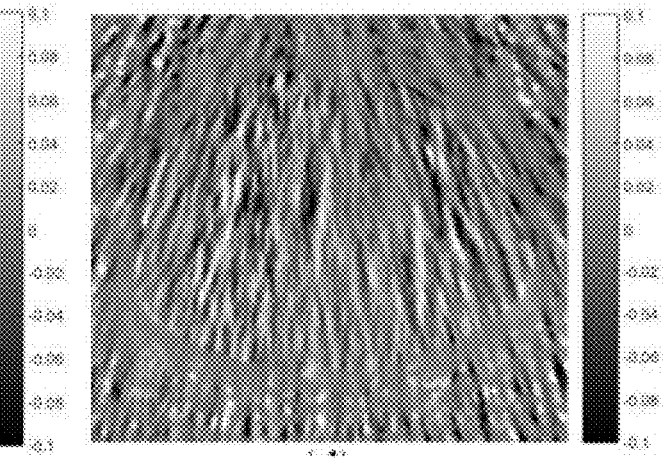
FIG. 8C              FIG. 8D

NORMALIZATION CRYSTAL EFFICIENCIES ESTIMATION FOR CONTINUOUS MOTION BED ACQUISITION

CROSS-REFERENCE TO RELATED APPLICATION

None.

FIELD

The present disclosure relates in general to patient-based detector crystal quality control for time-of-flight (TOF) data acquisition in continuous bed motion (CBM) acquisition. In particular, this disclosure relates to patient-based detector crystal quality control for TOF data acquisition in CBM acquisition in positron emission tomography (PET) systems.

BACKGROUND

PET scanner quality check control is performed on a daily basis. In Siemens scanners, for example, data is acquired from a uniform cylinder and the estimation of a crystal efficiency (CE) normalization component is carried out. Besides producing normalization array, the CEs analysis can also determine whether additional calibration should be performed.

PET is an imaging method that is used in nuclear medicine and radiation therapy. During PET, a positron is emitted inside the body of a patient subject being examined due to radioactive decay. The relevant radioactive decay may be induced, for example, by injection or inhalation of a radioactively marked radiopharmaceutical, such as a tracer. Disease information may be determined based on the spatial distribution of the tracer. After a short distance, the positron enters into interaction with an electron. The interaction destroys both particles. The destruction creates a pair of gamma quanta. The quanta are at an angle of 180° from one another. The gamma quanta penetrate the patient body and after exiting the body are recorded by two opposed detectors. A PET scanner for imaging includes a plurality of gamma radiation detectors, which surround the patient to be examined.

One of the physics ingredients of PET is scanner detector efficiencies, which are typically assumed to be known before image reconstruction. A component-based method is commonly used to model the normalization factors, which are the inverse of efficiencies for each Line-of-Response (LOR). A majority of components, such as geometric and crystal interference, are estimated once for a particular scanner type. Contrary to this, the crystal efficiency (CE) normalization component is estimated on a regular basis.

A number of methods to estimate CE normalization component have been developed. For example, the method from Defrise [M. Defrise, et al., "A Normalization Technique for 3D PET Data", *Phys. Med. Biol.*, 36, 939-952, 1991.] is an exact analytical method that typically uses only part of the available data. The fan sum method, which uses all available data, is not exact and might lead to bias in a very uneven efficiency distribution. CE normalization component can be estimated by the Maximum Likelihood (ML) approach. This approach has the advantage of versatility, where all available data are easily accommodated.

PET scanner calibration is a routine procedure that is usually performed daily in order to provide accurate results when a patient is subjected to a scan. In some scanners, for example, data are acquired for about 20 to 30 minutes each day using a phantom that is a 20 cm diameter uniform cylinder. By assuming a known object (e.g., the 20 cm diameter uniform cylinder) an estimation of a scintillation CE normalization component is conducted, since the rest of the normalization components are fixed for a given scanner type.

Normalization factors are corrections that compensate for non-uniformity of PET detector pair efficiencies. A component-based method is used to improve accuracy of the normalization factors. Most components, such as geometric and crystal interference components, can be estimated in advance for a particular scanner type. This is contrary to the scintillation CE normalization component, which is estimated on a regular basis. Besides producing a normalization array, the crystal efficiency values are used in daily Quality Control (QC) procedures. In this procedure, particular crystal block sensitivities are checked against the average scintillation detector crystal block sensitivity. A significant deviation from the average crystal block sensitivity will signal for replacement or monitoring of the particular crystal block. Potentially, data originating from this particular crystal block maybe excluded during list mode data histogramming and reconstruction. A scintillation detector crystal block is an array of crystals and consists of many crystals, each referred to as a pixel.

The use of frequent phantom scans is not ideal. Self-normalization (estimation of the normalization array from unknown object data) has been suggested as an alternative, but in non-TOF, an acceptable solution can be achieved only with the use of significant a priori knowledge. The TOF self-normalization problem was proposed in, where crystal efficiencies were estimated with the help of detector singles measurements. However, such measurements are not available on all scanners. Similar information can be extracted from random events data on Siemens scanners. However, this singles estimation is of a low count nature and is used for random variance reduction. Singles modeling is equivalent to a non-collimated single-photon emission computed tomography (SPECT) problem formulation. This requires the development of an additional reconstruction model. Finally, singles efficiencies may not correlate well with efficiencies for coincidence events in PET scanning.

Calibration is therefore complicated, since a phantom radioactive sources have to be set up in the treatment chamber and then removed. Such process requires manual intervention, involves cost, and can suffer from errors.

Inventor has previously provided a method for calibrating a PET detector by reconstructing the estimation of a scintillation CE normalization component simultaneously along with the reconstruction of the positron annihilation activity from TOF patient data. The method is described in United States patent publication No. 2015/0297168, the contents of which are incorporated herein by reference. The method allows monitoring of PET scanner performance as step-and-shoot (S&S) patient scans are performed, eliminating the need for the separate quality check scans.

In continuous bed motion (CBM) acquisition, however, the continuous motion of the patient may result in inaccuracies in the PET model for the normalization coefficient. Therefore, there is a need for improved methods for simultaneous monitoring of PET scanner's CEs normalization component in CBM acquisition mode.

SUMMARY

According to an aspect of the present disclosure, a method for simultaneously monitoring a PET scanner performance during a CBM acquisition, wherein the PET scanner has a patient bed that moves a patient in an axial motion through the PET scanner during the CBM acquisition is disclosed. The method comprising:

(a) generating time-of-flight (TOF) patient data of positron annihilation activity in a patient during the CBM acquisition, while accounting for the axial motion of the patient bed during the CBM acquisition, as a first data set;

(b) generating a complimentary data set by integrating the TOF patient data over the axial motion of the patient bed during the CBM acquisition; and (c) simultaneously reconstructing the positron annihilation activity and crystal efficiency normalization coefficient from the complimentary data set.

According to another aspect, a PET calibration system is disclosed. The PET calibration system comprising: a PET scanner having a patient bed that moves a patient in an axial motion through the PET scanner during the CBM acquisition; and a scintillation crystal efficiency calibration system that performs a method comprising:

(a) generating time-of-flight (TOF) patient data of positron annihilation activity in a patient during the CBM acquisition, while accounting for the axial motion of the patient bed during the CBM acquisition, as a first data set;

(b) generating a complimentary data set by integrating the TOF patient data over the axial motion of the patient bed during the CBM acquisition; and (c) simultaneously reconstructing the positron annihilation activity and crystal efficiency normalization coefficient from the complimentary data set.

According to another aspect, a non-transitory, machine readable storage medium encoded with computer program software, such that when a processor executes the computer program software, the processor performs a method for simultaneously monitoring a positron emission tomography (PET) scanner performance during a continuous-bed-motion (CBM) acquisition, wherein the PET scanner has a patient bed that moves a patient in an axial motion through the PET scanner during the CBM acquisition, the method comprising:

(a) generating time-of-flight (TOF) patient data of positron annihilation activity in a patient during the CBM acquisition, while accounting for the axial motion of the patient bed during the CBM acquisition, as a first data set;

(b) generating a complimentary data set by integrating the TOF patient data over the axial motion of the patient bed during the CBM acquisition; and (c) simultaneously reconstructing the positron annihilation activity and crystal efficiency normalization coefficient from the complimentary data set.

BRIEF DESCRIPTION OF THE DRAWINGS

The following will be apparent from elements of the figures, which are provided for illustrative purposes. The figures are schematic and are not necessarily to scale.

FIG. 6A shows patient activity by regular OSEM reconstruction with gold standard CE. FIG. 6B shows patient activity by ML-ACE reconstruction. FIG. 6C shows relative difference between 6A and 6B.

FIGS. 8A-8E represent patient activity and CE estimation reconstruction from defect-induced data.

DETAILED DESCRIPTION

Figure 1:
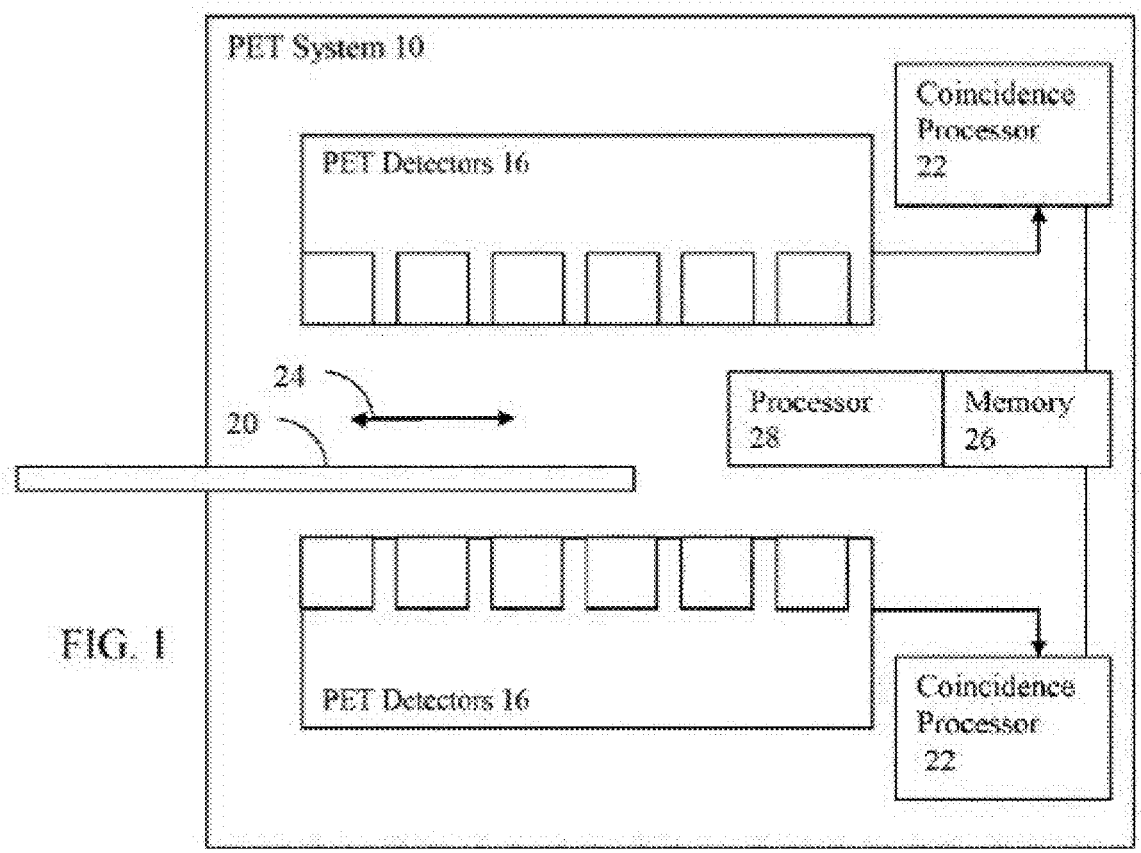
FIG. 1 illustrates a PET system featuring CBM acquisition in which the method of the present disclosure can be implemented.

This description of the exemplary embodiments is intended to be read in connection with the accompanying drawings, which are to be considered part of the entire written description.

In U.S. patent application publication No. 2015/0297168, the inventor disclosed a method for simultaneously reconstructing scintillation CE normalization component with the positron annihilation activity from TOF patient data acquired in S&S stationary acquisition. Therefore, scanner performance can be monitored as patient scans occur, eliminating the need for the frequent separate quality check scans using phantoms.

In the present disclosure, a method for simultaneous scanner performance monitoring (i.e. scanner calibration) during a CBM acquisition patient scanning is disclosed. In CBM data formation, counts from various detector pairs are combined together taking into account the axial bed motion. While it is beneficial for the positron annihilation activity reconstruction, axial CE structure is practically lost in corresponding computed normalization array due to averaging over the axial bed motion. As done in the S&S stationary acquisition disclosed in U.S. patent application publication No. 2015/0297168, additional complimentary data is generated during the CBM acquisition process. In the complimentary data set, the positron annihilation activity from TOF patient data is integrated over the axial bed motion, however CE structure is preserved. The same rebinner can be used to generate both data sets. Using two complimentary data sets, simultaneous reconstruction of the positron annihilation activity and scintillation CE normalization component from TOF patient data from the CBM acquisition process becomes practical. The algorithm can be interpreted as regular the positron annihilation activity maximum likelihood (ML) reconstruction with nested loop of scintillation CE normalization component estimation, which uses the same data which are compressed differently. By taking into consideration the TOF patient data integrated over the CBM acquisition motion, a simultaneous estimation can be made of the CBM acquisition patient image as well as the scintillation CE normalization coefficient.

Patient data from a Siemens mCT Flow scanner were used to validate the method's performance. The disclosed method produced CE maps similar to those of the daily scans using a phantom and therefore is suitable for a patient-based QC procedure.

Only CE normalization component needs to be estimated. This further significantly reduces the number of unknowns and solution sensitivity to noise, but requires development of specific reconstruction algorithms. The ML reconstruction of activity and crystal efficiency (A-CE) problem has additional aspects: the scattering event modeling takes part in the efficiencies estimation, and the model equations are non-linear with respect to scintillation CE with the known activity. What is attenuation and activity are defined up to scaling constant, since only their product is used in estimation. Thus, unknown global scaling is a lesser problem, since the average efficiency value is known due to the separate calibration of voxel activity to injected dose of the radioactive tracer.

Our investigations produced good results in the S&S stationary acquisition. CBM uses an acquisition generalization protocol where gamma ray detection counts from various detector pairs are combined together, taking into account the axial bed motion. While this is beneficial for activity reconstruction, axial CE structure is practically lost in the computed normalization array due to the averaging over the patient motion. According to an aspect of the present disclosure, additional data set, similar to the S&S data, is produced in order to estimate CE. In the additional data set (referred to hereafter as the complimentary data set), activity is integrated over the axial bed motion; however, the CE axial structure is preserved. In the previously known self-normalization methods, activity was assumed to be uniform after motion integration and an approximate fan-sum method was used to evaluate CE. The same implementation of rebinner can be used to generate both the CBM and S&S data sets. In the CBM case, the axial bed motion is integrated into the rebinning process, and in the S&S case, it is ignored. The rebinner software/hardware is optimized for data production and it is desirable to use its single version. Using two complimentary data sets, the simultaneous reconstruction of activity and CE is made to be practical in CBM.

CBM Acquisition in General

CBM acquisition performs a scan of the patient while the patient is moving through the PET system. PET measures the positron annihilation activity in the patient for each ring of detectors. For CBM, a given line-of-response (LOR) uses different detector pairs while the patient moves through the PET scanner. To normalize or scale each LOR for the corresponding detector pairs, the efficiency of the detector for the given detectors is estimated. By normalizing based on this efficiency, a more accurate measure of activity will result.

FIG. 1 shows a PET system 10 featuring CBM acquisition. The PET system 10 includes rings of detectors 16, a bed 20, coincidence processors 22, a memory 26, and a central controller 28. The central controller 28, memory 26, and/or a display are part of the PET system 10 or are separate (e.g., a computer or workstation). Additional, different, or fewer components may be provided. For example, the system is a computer without the detectors 16 and bed 20, instead relying on data acquired by a separate scanner. As another example, the PET system 10 includes power supplies, communications systems, and user interface systems.

The bed 20 is a gurney, table, or other support to hold an examination subject such as a patient. A robot, gears, cable, track, and/or other device moves the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems, such as a cylindrical or polar coordinate system, may be used.

The movement is continuous, at least during part of the scanning. The bed 20, while supporting the patient, is moved at a same or a varying velocity along the axial dimension 24. For example, the head of the patient is scanned with 1.5 mm/s movement of the patient, and the torso is scanned with 1.0 mm/s movement of the patient. Other combinations of the same or different rates, with or without a greater number of different velocities, may be used. The movement may pass the patient through the bore or merely partly into the bore. The movement is with or without acceleration. In one embodiment, the movement is back and forth, scanning the patient multiple times in a cyclical pattern. A single pass may be used in other embodiments.

The movement occurs during scanning (e.g., detection or measurement) by the detectors 16. The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
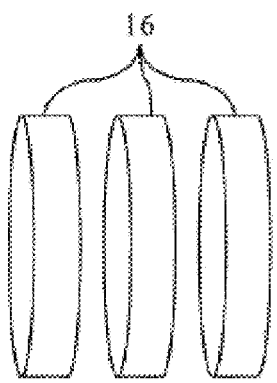
FIG. 2 represents blocks of detectors arranged as separate rings around the bore through which the patient bed moves during a CBM acquisition.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart, but are placed adjacent or abutting each other. Any gap may be provided between blocks within a ring, detectors within a block, and/or between rings. Any number of detectors in a block (e.g., 8 or 16), detector blocks in a ring, and/or rings may be used. The separate detectors 16 of each ring have their own singles rate and/or efficiency. The rings may extend completely or only partially around the bore.

The PET system 10 is a nuclear imaging system. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays.

As the bed 20 moves, the patient passes through the rings. A given part (e.g., organ) of the patient is within different rings at different times due to the continuous bed motion. The line-of-responses for the same part of the patient and corresponding actual three-dimensional location (i.e., point along the line-of-response) is at different locations at different times. The detectors 16 continue to detect gamma rays as the bed 20 and patient moves so different lines-of-response may be for the part of the patient at different positions within the bore.

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22. Pairs of gamma rays associated with a same positron emission are determined. Based on the detected event, an LOR is determined given the detectors involved in the detection of that event.

The detected events are passed to the memory 26 and/or the central controller 28. Alternatively, the coincidence processor 22 implements the computation of normalization coefficients rather than a separate processor 28. The central controller 28 connects with the detectors 16, such as through the coincidence processors 22.

The central controller 28 is a general processor, digital signal processor, graphics processing unit, application specific integrated circuit, field programmable gate array, digital circuit, analog circuit, combinations thereof, or other now known or later developed device for processing detected line-of-response events, computing normalization coefficients, normalizing, and/or reconstructing. The central controller 28 is a single device, a plurality of devices, or a network. For more than one device, parallel or sequential division of processing may be used. Different devices making up the processor 20 may perform different functions, such as one processor for calculating normalization coefficients and another processor for normalizing the line-of-response data. In one embodiment, the central controller 28 is a control processor or other processor of the PET system 10. In other embodiments, the central controller 28 is part of a separate workstation or computer.

The central controller 28 operates pursuant to stored instructions to perform various acts described herein, such as determining decay correction efficiency, determining a singles rate for a given time, determining detection time efficiency, calculating the normalization coefficients, normalizing the line-of-response data, and/or reconstruction. The central controller 28 is configured by software and/or hardware to perform any or all of the acts of the method summarized in FIG. 3.

Figure 3:
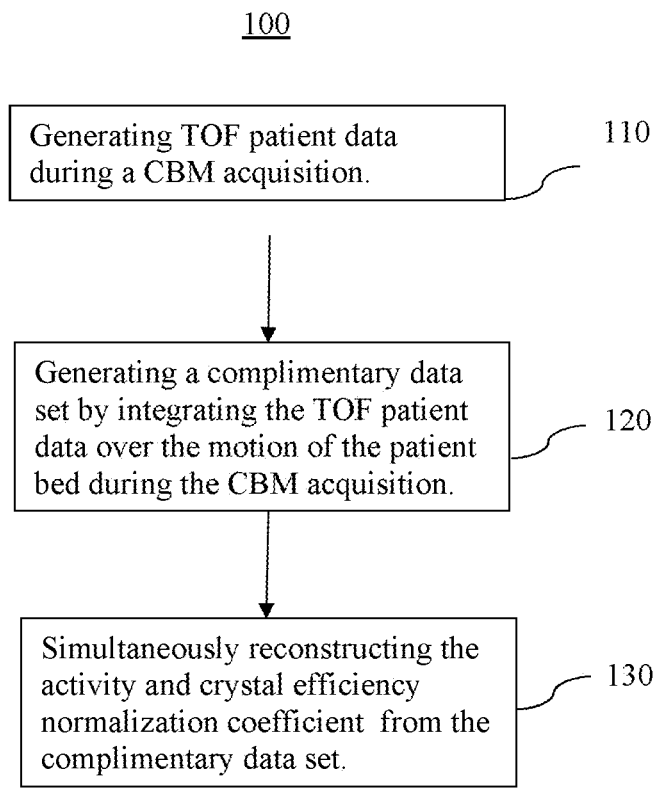
FIG. 3 is a flowchart illustrating the method for simultaneously monitoring a PET scanner performance during a CBM acquisition according to the present disclosure.

FIG. 3 is a flowchart 100 illustrating a method for simultaneously monitoring a PET scanner performance during a CBM acquisition, wherein the PET scanner has a patient bed that moves a patient in an axial bed motion through the PET scanner during the CBM acquisition. The method comprises (a) generating TOF patient data during the CBM acquisition, while accounting for the axial motion of the patient bed during the CBM acquisition, as a first data set (see Box 110); (b) generating a complimentary data set by integrating the TOF patient data over the axial motion of the patient bed during the CBM acquisition (see Box 120); and (c) simultaneously reconstructing the activity and crystal efficiency normalization coefficient from the complimentary data set (see Box 130).

The operation and configuration of the central controller 28 is first described in general below. One example implementation is described in more detail in the following discussion.

The central controller 28 is configured to determine normalization coefficients. The weighting to account for differences in efficiency for detecting different lines of response relative to the patient is calculated. In CBM, the lines-of-response change axial position over time when considered relative to the patient. As a result, various detector pairs and other factors contribute to the efficiency of detection. These factors, which may vary over time, are included in the computation of the normalization coefficients.

The central controller 28 accounts for the decay. A decay correction efficiency is determined for an isotope used during the PET scan. The isotope's decay characteristic changes over time. This variation in decay is used for the decay correction efficiency.

The central controller 28 accounts for the velocity variation of the bed and patient. As the velocity of the bed changes, the detection time efficiency changes. The detection time efficiency at different times and corresponding positions of the bed or patient during the PET scan is determined based, in part, on the velocity.

The central controller 28 may account for other factors as well, such as the time variation of the singles rate and/or normalization of the scanner (e.g., normalization used in S&S or other scanning protocols without the axial bed motion during the scan).

The central controller 28 applies the normalization coefficients. For each given LOR, the activity is weighted by the normalization coefficient for that LOR. The central controller 28 or another processor may reconstruct the object space from the normalized LOR.

The central controller 28 uses the events (e.g., line-of-response events), empirical information (e.g., global singles rate), and/or known information (e.g., decay correction constant) stored in the memory 26 for processing. For processing, the data bypasses the memory 26, is temporarily stored in the memory 26, or is loaded from the memory 26.

The detected events, LOR information (e.g., sinograms), time step, singles rate, decay information, scanner normalization information, CBM normalization coefficients, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 10 or a remote workstation or database, such as a PACS memory.

The memory 26 is additionally or alternatively a non-transitory computer readable storage medium with processing instructions. The memory 26 stores data representing instructions executable by the programmed central controller 28 for computing normalization coefficients in continuous bed motion acquisition. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 10 may include a display. For example, the central controller 28 reconstructs the patient or object being scanned from the normalized line-of-response data. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

CBM Data Rebinning

Figure 4A:
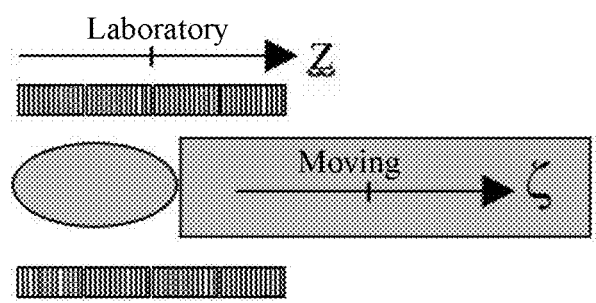
FIGS. 4A and 4B illustrate the two systems of coordinates in CBM acquisition. Only the axial axis is shown.
Figure 4B:
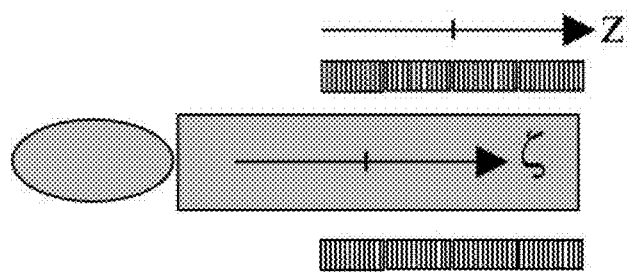

The method for simultaneous scanner performance monitoring during a patient scanning by CBM acquisition according to an aspect of the present disclosure involves CBM Data Rebinning. There are two systems of coordinates in CBM acquisition as illustrated in FIGS. 4A and 4B. Only the axial axis of the patient bed is shown. One is laboratory, which is aligned with a scanner. The second is moving, where the object is stationary. The CBM scanner data are represented by transaxial radial coordinate ρ, azimuthal coordinate θ, and axial plane coordinate z, which includes a polar angle. The moving object virtual LORs have the same transaxial coordinates, but are described by different axial coordinate ζ. Let us denote a function in which we map coordinate ζ onto the scanner system coordinate as Z(ζ,t). This function uses object/bed axial motion knowledge. The function aligns laboratory and moving system axial coordinates with the nearest neighbor approximation in order to preserve Poisson statistics during data rebinning. The rebinner produces two types of data: one data set for A (activity reconstruction) and a complimentary data set for CE estimations.

Activity Reconstruction Step

TOF prompt CBM data y with spatial projection index j=(ρ, θ, ζ) and TOF bin index T can be modeled by combining the true events (unscattered gamma coincidence events) modeled projection $\bar{p}$ from the emission object f, defined by voxel index k, corrected for scanner efficiency through a normalization array n for attenuation by a, and scatter estimation S, corrected for scanner efficiency as well, and mean random data $\bar{r}$:

$$\bar{y}_{\rho\theta\zeta T} = a_{\rho\theta\zeta} n_{\rho\theta\zeta}^{-1}(\varepsilon) \sum_k C_{\rho\theta\zeta T,k} f_k + n_{\rho\theta\zeta}^{-1} S_{\rho\theta\zeta T} + \bar{r}_{\rho\theta\zeta T} = \quad (1)$$

$$a_{\rho\theta\zeta} n_{\rho\theta\zeta}^{-1}(\varepsilon) \bar{p}_{\rho\theta\zeta T} + n_{\rho\theta\zeta}^{-1} S_{\rho\theta\zeta T} + \bar{r}_{\rho\theta\zeta T}$$

where C is the geometrical projection system matrix, which contains probabilities to detect coincidence event at (ρ, θ, ζ) originated at activity array voxel k, and ε is the crystal efficiency. The CBM data normalization (denoted by coordinate ζ) is computed (integrated over time) from scanner normalization factors accounting for the axial movement during CBM according to:

$$n_{\rho\theta\zeta}^{-1} = \int_0^{t_{acq}} dt \sum_z e^{-\lambda t} d_{\rho\theta z}(t) n_{\rho\theta z}^{-1} \delta_{z,Z(\zeta,t)} \quad (2)$$

where λ is the decay correction constant for a specific isotope, δ is Kronecker's delta, d is the dead time correction factor, and $t_{acq}$ is CBM acquisition time. Dead time correction, which accommodates for signal loss when detector processes relatively high count rate, is time dependent due to the variable single rate. Equation (2) describes the averaging process of virtual LOR efficiency over scanner LOR efficiencies and is discussed in more detail by the inventor in V. Y. Panin, A. M. Smith, J. Hu, F. Kehren and M. E. Casey, "Continuous bed motion on clinical scanner: Design, Data Correction and Reconstruction", *Phys. Med. Bio.*, vol. 59, pp. 6153-6174, 2014.

The scanner normalization factors (denoted by coordinate z) may accommodate for the mashing and rebinning of the LORs, as with Siemens scanners, connecting two detector crystals i and i' into projection bin:

$$n_{\rho\theta z}^{-1}(\varepsilon) = \sum_{i,i'} \omega_{\rho\theta z,ii'} g_{ii'} \varepsilon_i \varepsilon_{i'}, \quad (3)$$

where g is the geometrical component of the normalization array. The ω is the LOR contribution factor into projection data due to mashing and spanning data compression techniques, where ω is defined by the following:

$$\omega_{j,ii'} = \begin{cases} 1/2, & \text{if } ii' \text{ contribute to sinogram bin } j \\ 0, & \text{otherwise} \end{cases} \quad (4)$$

Due to integration over axial movement in (2), the CBM normalization array loses information about the axial CE structure. Therefore, the described data set is used for activity reconstruction, assuming known CEs.

CE Estimation Step (the CE-Step)

The complimentary data set, acquired in a stationary system of coordinate, prompt data, is modeled as follows:

$$\bar{y}_{\rho\theta zT} = n_{\rho\theta z}^{-1}(\varepsilon) B\left(a_{\rho\theta\zeta} \sum_k C_{\rho\theta\zeta T,k} f_k\right) + n_{\rho\theta z}^{-1}(\varepsilon) B(S_{\rho\theta\zeta T}) + \bar{r}_{\rho\theta zT} = \quad (5)$$

$$n_{\rho\theta z}^{-1}(\varepsilon) \bar{p}_{\rho\theta zT} + n_{\rho\theta z}^{-1}(\varepsilon) S_{\rho\theta zT} + \bar{r}_{\rho\theta zT},$$

where the motion blurring operator $y_{\rho\theta z}$ can be denoted as $$y_{\rho\theta z} = B(y_{\rho\theta\zeta}) = \int_0^{t_{acq}} dt \sum_\zeta e^{-\lambda t} d_{\rho\theta z}(t) y_{\rho\theta\zeta} \delta_{z,Z(\zeta,t)}. \quad (6)$$

Note that the definition of the CE-step modeled true $\bar{p}$ includes attenuation in the blurring operation. Due to integration over movement in (6), the axial structure of the activity distribution will be lost.

The total acquisition time can be different between (2) and (6), since modeling in (5) should not include projection outside the axial range of the reconstructed activity field-of-view (FOV). Random means are different between the two data sets as well and are estimated differently from delay events.

ML-ACE Algorithm

Figure 5:
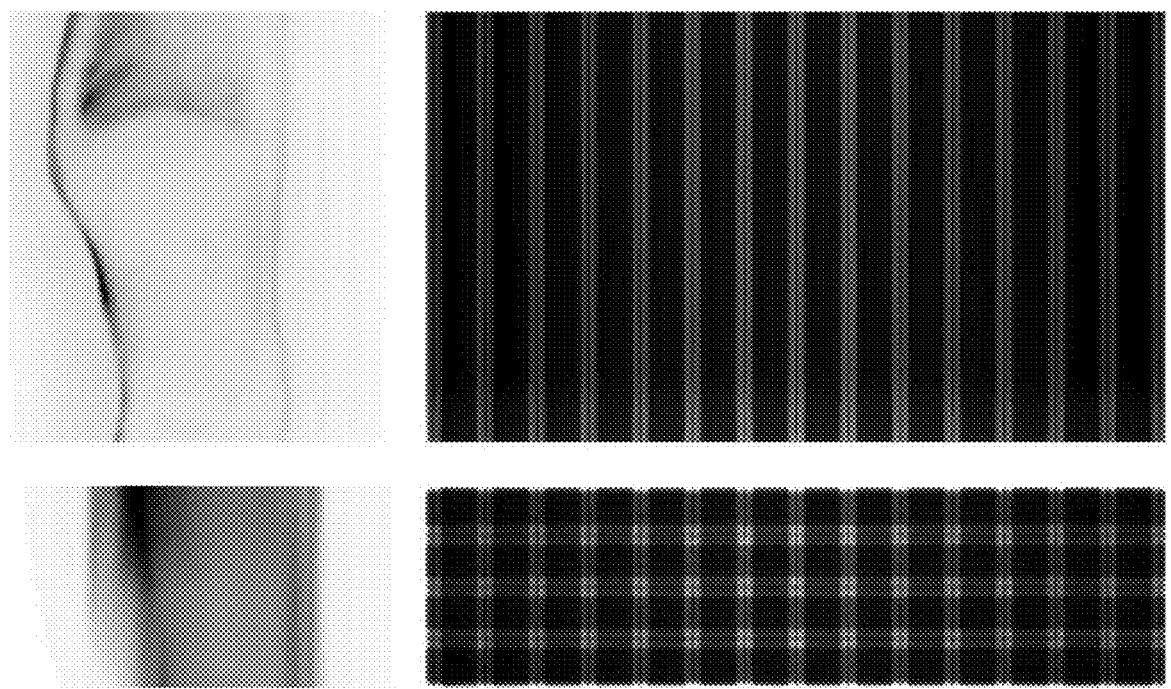
FIG. 5 shows data sets used in ML-ACE algorithm steps.

Simultaneous activity and crystal efficiency normalization component reconstruction (A-CE) can be carried out using the two data sets shown in FIG. 5. In FIG. 5, the first column represents modeled activity projection. The second column represents normalization array, direct planes. The first row is the activity reconstruction step (A-step) and the second row is the CE normalization component reconstruction step (CE-step). Vertical axis is axial direction. The optimization is performed by iterations; each is divided into the two steps described above. The A-step is the activity update with the fixed normalization (efficiencies) array, where CBM TOF data are used. A commonly used ordered subsets expectation maximization (OS-EM) algorithm. The following objective function $$L_A(f) = \sum_{j=\{\rho\theta\zeta\},T} (y_{jT} \ln(\bar{y}_{jT}) - \bar{y}_{jT})$$

is to be maximized w.r.t. f where f is activity image as defined in (1).

The CE-step is the efficiencies updated by the iterative algorithm described in V. Y. Panin, "Monotonic Iterative Algorithms for Crystal Efficiencies Estimation from Normalization Data and Single Rates Estimation from Compressed Random Coincidence Data," 2013 *IEEE Nucl. Sci. Symp. and Med. Imag. Conf.* (Seoul, Korea), M23-1, 2013, where the motion blurred activity and scatter distributions will be known from the A-step. In this step, complimentary TOF or non-TOF data are used and four iterations are performed in the estimation of CE. Here, the goal is maximization of the following objective function:

$$L_{CE}(\varepsilon) = \sum_{j=\{\rho\theta z\},T} (y_{jT} \ln(\bar{y}_{jT}) - \bar{y}_{jT}) \ w.r.t. \ \varepsilon.$$

The CE-step updated equations are provided for completeness:

$$\varepsilon_i^{(m+1)} = \frac{-B_i + \sqrt{B_i^2 + 4A_i C_i}}{2A_i} \quad (7)$$

$$A_i = \sum_j \sum_{i'} \omega_{j,ii'} g_{ii'} (\bar{p}_j(f) + S_j),$$

$$B_i = \sum_j \sum_{i'} \omega_{j,ii'} (\bar{p}_j(f) + S_j) \varepsilon_{i'}^{(m)} - A_i \varepsilon_i^{(m)}$$

$$C_i = \varepsilon_i^{(m)} \sum_{jT} \frac{y_{jT}}{\bar{y}_{jT}^{(m)}(f, \varepsilon^{(m)})} \sum_{i'} \omega_{j,ii'} (\bar{p}_{jT}(f) + S_{jT}) \varepsilon_{i'}^{(m)}$$

$$j = \{\rho\theta z\}$$

where m is the iteration number for the updating the crystal efficiency ε. Note that TOF information was eliminated in the computing of A and B, where $\bar{p}_j$ and $S_j$ represent summation of $\bar{p}_{jT}$ and $S_{jT}$ over TOF bin index T However, TOF information is preserved in the computing of C. If non-TOF data are used in the CE-step, then the computing of C has no summation over the T index.

Each step uses a simultaneous monotonic update algorithm. The two steps together, however, can represent the sequential update method. The method can be interpreted as regular activity ML reconstruction with a nested loop of CE normalization component estimation, which uses effectively the same data yet is compressed differently. In the following TOF/non-TOF nested loop, ML-ACE will denote CE normalization component estimations from TOF/non-TOF CE-step data.

The ML-ACE initial condition was CE initiated by the average block values and uniform activity distribution. Three iterations of the sequential update method were performed. This effectively resulted in three iterations and 21 subsets of OS-EM activity reconstruction and 12 iterations of CE normalization component estimation.

Figure 9:
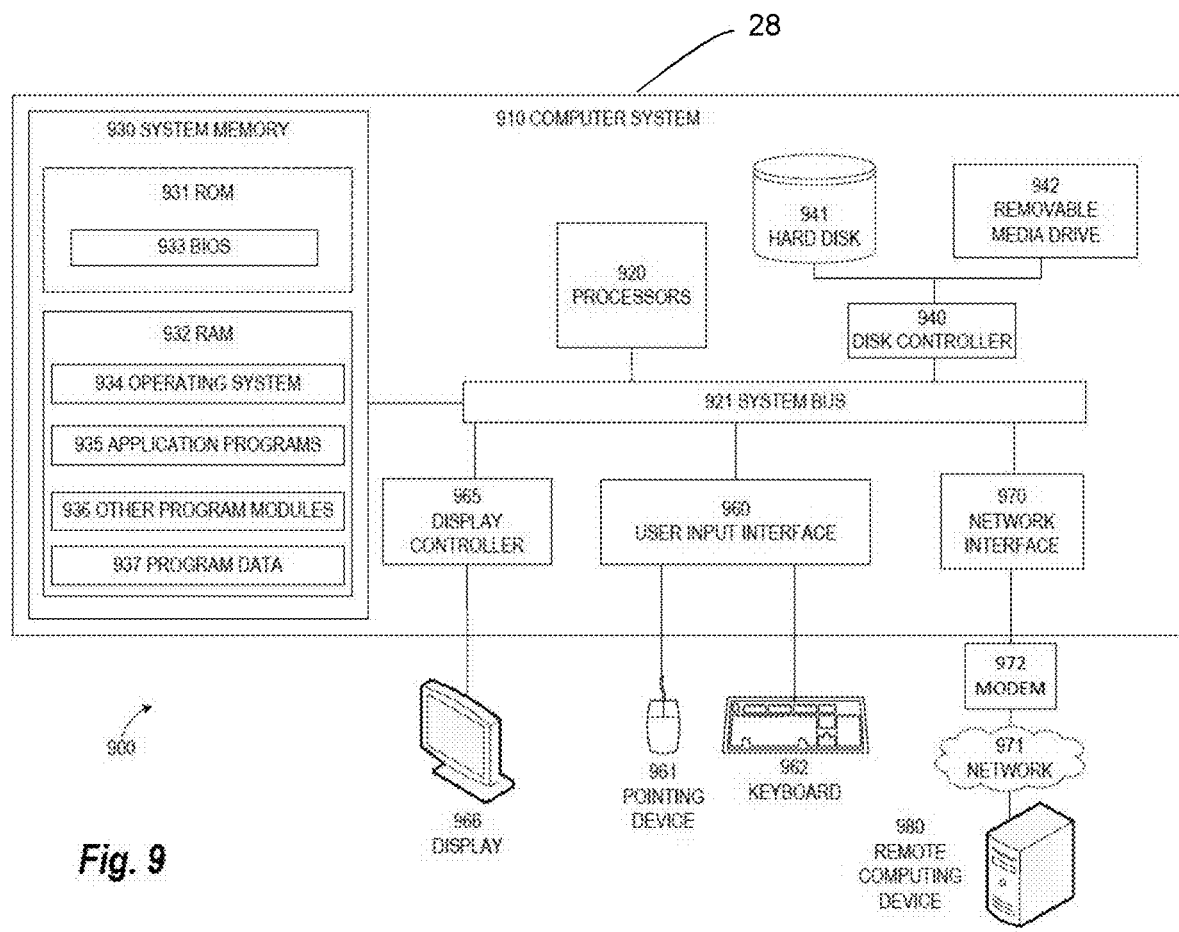
FIG. 9 is a detailed block diagram of an example of the computer system suitable for the system of FIG. 1, according to some embodiments.

FIG. 9 illustrates an exemplary computing environment 900 within which includes an embodiments of the central controller 28 of FIG. 1. For example, computing environment 900 can be used to implement the method disclosed herein. Computers and computing environments, such as central controller 28 and computing environment 900, are known to those of skill in the art and thus are described briefly here.

As shown in FIG. 9, the central controller 28 can include a communication mechanism such as a system bus 921 or other communication mechanism for communicating information within the central controller 28. The central controller 28 further includes one or more processors 920 coupled with the system bus 921 for processing the information.

The processors 920 can include one or more central processing units (CPUs), graphical processing units (GPUs), or any other processor known in the art. More generally, a processor can include a device for executing machine-readable instructions stored on a computer readable medium, for performing tasks and can comprise any one or combination of, hardware and firmware. A processor can also comprise memory storing machine-readable instructions executable for performing tasks. A processor acts upon information by manipulating, analyzing, modifying, converting or transmitting information for use by an executable procedure or an information device, and/or by routing the information to an output device. A processor can use or comprise the capabilities of a computer, controller or microprocessor, for example, and be conditioned using executable instructions to perform special purpose functions not performed by a general purpose computer. A processor can be coupled (electrically and/or as comprising executable components) with any other processor enabling interaction and/or communication there-between. A user interface processor or generator can include electronic circuitry or software or a combination of both for generating display images or portions thereof. A user interface can comprise one or more display images enabling user interaction with a processor or other device Continuing with reference to FIG. 9, the central controller 28 also includes a system memory 930 coupled to the system bus 921 for storing information and instructions to be executed by processors 920. The system memory 930 can include computer readable storage media in the form of volatile and/or nonvolatile memory, such as read only memory (ROM) 931 and/or random access memory (RAM) 932. The RAM 932 can include other dynamic storage device(s) (e.g., dynamic RAM, static RAM, and synchronous DRAM). The ROM 931 can include other static storage device(s) (e.g., programmable ROM, erasable PROM, and electrically erasable PROM). In addition, the system memory 930 can be used for storing temporary variables or other intermediate information during the execution of instructions by the processors 920. A basic input/output system 933 (BIOS) containing the basic routines that help to transfer information between elements within central controller 28, such as during start-up, can be stored in the ROM 931. RAM 932 can contain data and/or program modules that are immediately accessible to and/or presently being operated on by the processors 920. System memory 930 can additionally include, for example, operating system 934, application programs 935, other program modules 936 and program data 937.

The central controller 28 can also include a disk controller 940 coupled to the system bus 921 to control one or more storage devices for storing information and instructions, such as a magnetic hard disk 941 and a removable media drive 942 (e.g., floppy disk drive, compact disc drive, tape drive, and/or solid state drive). Storage devices can be added to the central controller 28 using an appropriate device interface (e.g., a small computer system interface (SCSI), integrated device electronics (IDE), Universal Serial Bus (USB), or FireWire).

The central controller 28 can also include a display controller 965 coupled to the system bus 921 to control a display or monitor 966, such as a liquid crystal display (LCD), for displaying information to a computer user. The computer system includes an input interface 960 and one or more input devices, such as a keyboard 962 and a pointing device 961, for interacting with a computer user and providing information to the processors 920. The pointing device 961, for example, can be a mouse, a light pen, a trackball, or a joy stick for communicating direction information and command selections to the processors 920 and for controlling cursor movement on the display 966. The display 966 can provide a touch screen interface which allows input to supplement or replace the communication of direction information and command selections by the pointing device 961.

The central controller 28 can perform a portion or all of the processing steps of embodiments in response to the processors 920 executing one or more sequences of one or more instructions contained in a memory, such as the system memory 930. Such instructions can be read into the system memory 930 from another computer readable medium, such as a magnetic hard disk 941 or a removable media drive 942. The magnetic hard disk 941 can contain one or more data stores and data files used by various embodiments. Data store contents and data files can be encrypted to improve security. The processors 920 can also be employed in a multi-processing arrangement to execute the one or more sequences of instructions contained in system memory 930. In alternative embodiments, hard-wired circuitry can be used in place of or in combination with software instructions. Thus, embodiments are not limited to any specific combination of hardware circuitry and software.

Some embodiments include software instructions written in a high level language, such as C, C++, C#, Java, Fortran or Python. Some embodiments are written for a multi-paradigm numerical computing environment, such as Matlab, sold by Mathworks, Inc. of Natick, Mass., or the like.

As stated above, the central controller 28 can include at least one computer readable medium or memory for holding instructions and for containing data structures, tables, records, or other data described herein. The term "computer readable medium" as used herein refers to any non-transitory machine-readable storage medium that participates in providing instructions to the processors 920 for execution. A computer readable medium can take many forms including, but not limited to, non-transitory, non-volatile media and volatile media. Non-limiting examples of non-volatile media include optical disks, solid state drives, magnetic disks, and magneto-optical disks, such as magnetic hard disk 941 or removable media drive 942. Non-limiting examples of volatile media include dynamic memory, such as dynamic random access memory 930.

The central controller 28 can operate in a networked environment using logical connections to one or more remote computers, such as remote computing device 980. Remote computing device 980 can be a personal computer (laptop or desktop), a mobile device, a server, a router, a network PC, a peer device or other common network node, and typically includes many or all of the elements described above relative to central controller 28. When used in a networking environment, central controller 28 can include modem 972 for establishing communications over a network 971, such as the Internet. Modem 972 can be connected to system bus 921 via user network interface 970, or via another appropriate mechanism.

Network 971 can include, but is not limited to, the Internet, an intranet, a local area network (LAN), a wide area network (WAN), a metropolitan area network (MAN), a personal area network (PAN) a direct connection or series of connections, a cellular telephone network, or any other network or medium capable of facilitating communication between central controller 28 and other computers (e.g., remote computing device 980). The network 971 can be wired, wireless or a combination thereof. Wired connections can be implemented using Ethernet, Universal Serial Bus (USB), RJ-6, or any other wired connection. Wireless connections can be implemented using Wi-Fi, WiMAX, and Bluetooth, infrared, cellular networks, satellite or any other wireless connection methodology. Additionally, several networks can work alone or in communication with each other to facilitate communication in the network 971.

The functions and process steps described herein can be performed automatically or wholly or partially in response to user command. An activity (including a step) performed automatically is performed in response to one or more executable instructions or device operation without user direct initiation of the activity.

The methods and system described herein can be at least partially embodied in the form of computer-implemented processes and apparatus for practicing those processes. The disclosed methods can also be at least partially embodied in the form of tangible, non-transitory machine readable storage media encoded with computer program code. The media can include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods can also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods can alternatively be at least partially embodied in a digital signal processor formed of application specific integrated circuits for performing the methods.

Therefore, according to an aspect of the present disclosure, a non-transitory, machine readable storage medium encoded with computer program software, such that when a processor executes the computer program software, the processor performs a method for simultaneously monitoring a positron emission tomography (PET) scanner performance during a continuous-bed-motion (CBM) acquisition is disclosed, wherein the PET scanner has a patient bed that moves a patient in an axial motion through the PET scanner during the CBM acquisition, the method comprising:

(a) generating time-of-flight (TOF) patient data during the CBM acquisition, while accounting for the axial motion of the patient bed during the CBM acquisition, as a first data set;

(b) generating a complimentary data set by integrating the TOF patient data over the axial motion of the patient bed during the CBM acquisition; and (c) simultaneously reconstructing the activity and crystal efficiency normalization coefficient from the complimentary data set.

Experimental Data

The method of the present disclosure was verified on Siemens mCT Flow patient data acquired with 0.8 mm/sec bed speed in list mode. During histogramming of the list mode file, a fraction of counts acquired on LORs that originated in the four blocks was withdrawn. This artificially created hot spots in the affected block's CE map. The central crystals maintained original efficiency, while the rest of the crystals lost 50% of their original efficiency. This data set will be denoted as the one with defects present. A defect-absent (all counts used) data set was produced as well.

The gold standard CE normalization component estimation was extracted from the daily QC normalization file. Note that the coordinate ascent algorithm is used in Siemens daily QC software for CE normalization component estimations, making direct comparison with ML-ACE results difficult.

The 233 planes of image data, which corresponds to an axial extend of three mCT S&S acquisitions, was reconstructed. Scatter was estimated using the gold standard CE normalization component estimation and was fixed in investigation. Attenuation was produced in a regular way based on the CT scan. Dead time and decay corrections were ignored in normalization array computations. A-step CBM random data were used as-is, while CE-step random data underwent a random smoothing procedure with 50 iterations of monotonic algorithm.

In the A-step, CBM data were reconstructed all at once, resulting in production of a single image. In other words, a data chunking scheme was not used, contrary to clinical environment reconstruction. The image was rescaled according to the total activity of the gold standard image, which was 3 iterations of OSEM reconstruction using daily QC CE normalization. While activity and CE each can be rescaled consistently so that modeled projections will maintain their original scales, this did not hold true for the scatter component. Scatter was constant during the investigations and CE scaling affected its scale In the CE-step, all available data were used. Outside of the true events support, CE are modeled through scatter components. True events modeled projections were zeroed outside the patient boundary (image support is derived from the CT-based attenuation map) before implementing the blurring operator (5). The blurring operator (5) is a simple summation over modeled projection planes.

The activity reconstructions were 400×400×233 (image volume in 400 voxel in xy direction and y direction and 233 voxel in axial, z, direction), 2×2×2 mm (each voxel size, apparently cubic one). The four ring mCT scanner consists of 48 transaxial blocks (horizontal direction in the following figures) and 4 axial blocks (vertical). Each of the 48 blocks contains 13×13 crystals (4×4×2 mm each). Therefore, the CE array consists of 624×52 detectors.

For presentation of a defective data set, a CE contrast-noise trade-off curve was built. Recovery of hot spots was computed as the ratio of the central crystals in an affected block to the central crystals of a neighboring block. Recovery was averaged over all four affected blocks. In order to understand the noise property, we computed the standard deviation of each crystal efficiency in one block (total 13×13 crystals) over all 48 transaxial blocks, normalized by the average block efficiency value. Noise was computed as the average standard deviation over all 13×13 crystals. Forty blocks (10×4) were used in the noise assessment. Recovery of hot spots versus noise in the crystal efficiencies estimation was considered as a function of the iteration number to understand the algorithm convergence property.

Results

Figure 6A:
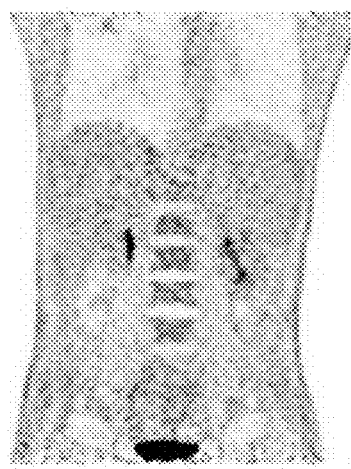
FIGS. 6A, 6B, and 6C show patient activity reconstruction.
Figure 6B:
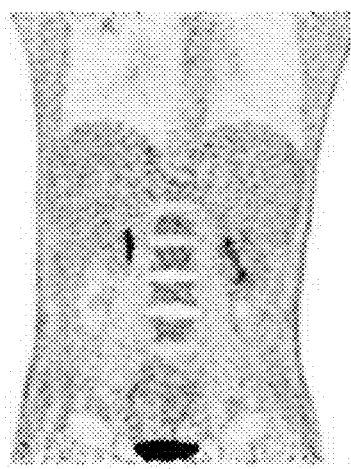
Figure 6C:
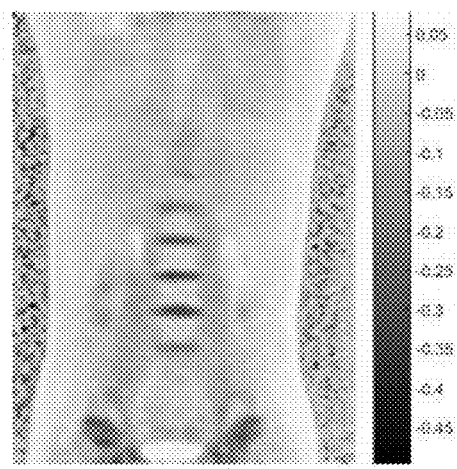

FIGS. 6A-6C show patient activity reconstructions created by the OSEM reconstruction algorithm using daily QC CE, and by ML-ACE from defect-absent data. FIG. 6A shows patient activity by regular OSEM reconstruction with gold standard. FIG. 6B shows patient activity by ML-ACE reconstruction. FIG. 6C shows the relative difference between the patient activities shown in FIG. 6A and FIG. 6B. Visually these images were practically of identical quality. Nevertheless, the relative difference image, FIG. 6C, reveals that there was a difference in cold spots, such as the outside of the patient support. In regular uptake regions the difference was relatively small, around 5-7%.

Figure 7A:
FIG. 7A shows the gold standard CE from a scan.
Figure 7B:
FIG. 7B shows CE of ML-ACE reconstruction.
Figure 7C:
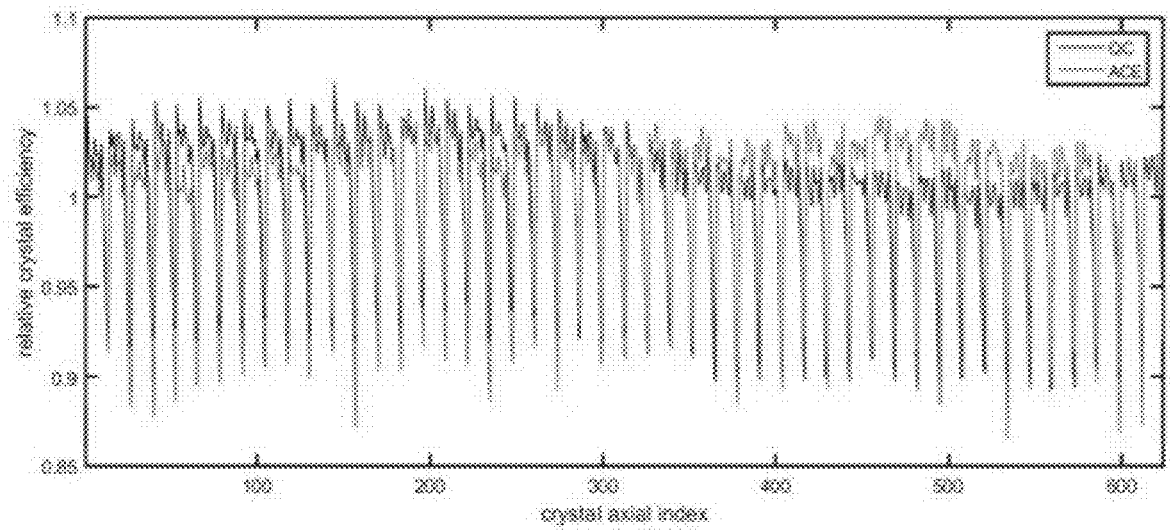
FIG. 7C shows CE normalized transaxial profile, averaged over axial dimension.

The corresponding ML-ACE crystal efficiencies estimations are presented in FIGS. 7A-7C along with the gold standard, daily QC CE. FIG. 7A shows the gold standard crystal efficiencies from morning scan. FIG. 7B shows CE of ML-ACE reconstruction. FIG. 7C shows CE normalized transaxial profile, averaged over axial dimension. The black curve in the graph in FIG. 7C represents gold standard QC CE, and the gray curve represents ML-ACE CE. The noise level appears to be less compared to that of the gold standard estimation due to a difference in CE estimation algorithms. Both efficiency distributions displayed a similar uncommon block pattern of certain crystals. Overall the CE estimation uniformity was satisfactory, according to FIG. 7C. We observed that random smoothing and zeroing of residual reconstruction activity outside of patient boundaries was essential in assuring overall CE estimation uniformity.

Figure 8E:
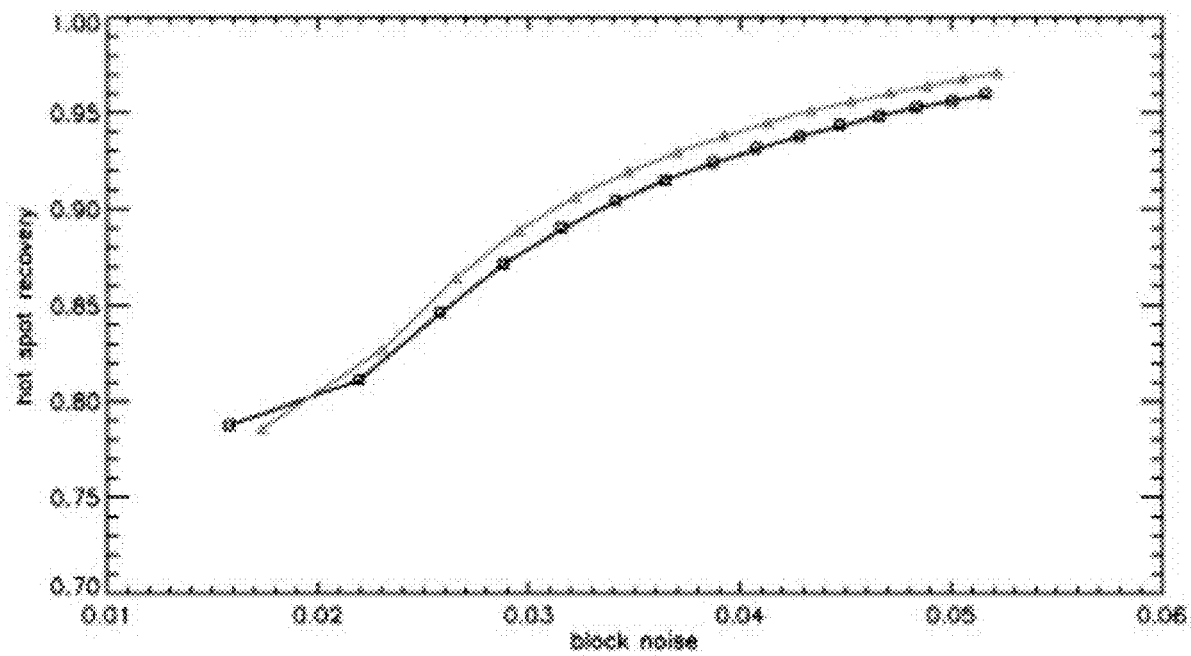

FIGS. 8A-8E represent patient activity and CE estimation reconstructions from defect-induced (i.e. defect-present) data. FIG. 8A shows ML-ACE reconstructed CE. FIG. 8B shows patient transaxial slices used in generating the FIGS. 8C and 8D. FIG. 8C shows an image of relative difference between OSEM reconstruction using daily QC normalization from defect-free and defect-induced data. FIG. 8D shows an image of relative difference between ML-ACE reconstruction from defect-free and defect-induced data. The influence of normalization mismatch was relatively mild. This supports the currently well-known fact that TOF reconstruction significantly reduces correction factor mismatch related artifacts. The ML-ACE reconstruction correctly identified CE defects, see FIG. 8A. The differences in ML-ACE activity reconstruction from defect-present and defect-absent data were less localized compared with the use of OS-EM; see FIGS. 8C and 8D. FIG. 8E shows CE hot spot recovery versus noise. In the graph of FIG. 8E, the black curve represents non-TOF nested loop ML-ACE reconstruction, and the red curve represents TOF nested loop ML-ACE reconstruction. FIG. 8E demonstrates that there was a benefit, through relatively small, in the TOF (rather than smaller size data in non-TOF) CE nested loop of ML-ACE.

We observed that one ML-ACE iteration, consisting of the A-step and CE-step, resulted in a total image value reduction by about 20% before rescaling to the correct value. In our experience, ML-ACF and ML-ACE scale instability was observed in computer simulations when significant noise level was simulated. Unlike ML-ACF, CE was a multiplication factor for the scatter component. The scatter component was fixed in investigations and did not follow the rescaling of activity. This likely explains the cold spot difference between OS-EM and ML-ACE. ML-ACF was effectively slightly more scatter corrected, resulting in colder cold spots.

We have investigated various projection data radial domains (defined by block to block coincidence pairs) used in the CE-step. For example, only the sinogram central part, where the true event has a major contribution, i.e. where scattered events can be ignored, can be used for the CE estimation.

FIG. 8E demonstrates that there was relatively small benefit in the TOF nested loop of ML-ACE. Therefore, production of non-TOF data for the CE step seems to be a more attractive option from a practical point of view.

The proposed CE estimation scheme is applicable for the daily QC procedure (known activity object) as well. Here only object position, especially in the axial direction, will need to be determined from the A-step. The axially short object can be used in CBM acquisition coverage of the whole FOV. This phantom will be easier to manufacture and handle during the daily routine.

CBM patient self-normalization and QC are feasible with the help of additional data rebinning. Patient data from a Siemens mCT scanner were used to validate the proposed scheme. Initial investigations showed the proposed method can produce crystal efficiencies maps comparable to those of the daily phantom scans and therefore is suitable for a patient based QC procedure.

The description of the various embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method for simultaneously monitoring a positron emission tomography (PET) scanner performance during a continuous-bed-motion (CBM) acquisition, wherein the PET scanner has a patient bed that moves a patient in an axial motion through the PET scanner during the CBM acquisition, the method comprising:
   (a) generating time-of-flight (TOF) patient data of positron annihilation activity in a patient during the CBM acquisition, while accounting for the axial motion of the patient bed during the CBM acquisition, as a first data set;
   (b) generating a complimentary data set by integrating the TOF patient data over the axial motion of the patient bed during the CBM acquisition, wherein the complimentary data set is modeled by the equation:

$$\bar{y}_{\rho\theta zT} = n^{-1}_{\rho\theta z}(\varepsilon) B\left(a_{\rho\theta\zeta} \sum_k C_{\rho\theta\zeta T,k} f_k\right) + n^{-1}_{\rho\theta z}(\varepsilon) B(S_{\rho\theta\zeta T}) + \bar{r}_{\rho\theta zT} =$$
$$n^{-1}_{\rho\theta z}(\varepsilon)\bar{p}_{\rho\theta zT} + n^{-1}_{\rho\theta z}(\varepsilon)S_{\rho\theta zT} + \bar{r}_{\rho\theta zT},$$

wherein $y_{\rho\theta z}$, a motion blurring operator, is calculated by:

$$y_{\rho\theta z} = B(y_{\rho\theta\zeta}) = \int_0^{t'_{acq}} dt' \sum_{\zeta} e^{-\lambda t} d_{\rho\theta z}(t) y_{\rho\theta\zeta} \delta_{z,Z(\zeta,t)};$$

and
   (c) simultaneously reconstructing the positron annihilation activity and crystal efficiency normalization coefficient from the complimentary data set.

2. The method of claim 1, wherein the step (a) comprises CBM data y with spatial projection index j=(ρ, θ, ζ) and TOF bin index T is modeled by combining the true events modeled projection $\bar{p}$ from the emission object f, defined by voxel index k, corrected for scanner efficiency through a normalization array n for attenuation by a, and scatter estimation S, corrected for scanner efficiency, and mean random data $\bar{r}$:

$$\bar{y}_{\rho\theta\zeta T} = a_{\rho\theta\zeta} n^{-1}_{\rho\theta\zeta}(\varepsilon) \sum_k C_{\rho\theta\zeta T,k} f_k + n^{-1}_{\rho\theta\zeta} S_{\rho\theta\zeta T} + \bar{r}_{\rho\theta\zeta T} =$$
$$a_{\rho\theta\zeta} n^{-1}_{\rho\theta\zeta}(\varepsilon)\bar{p}_{\rho\theta\zeta T} + n^{-1}_{\rho\theta\zeta} S_{\rho\theta\zeta T} + \bar{r}_{\rho\theta\zeta T};$$

wherein C is the geometrical projection system matrix;
wherein ε is the crystal efficiency; and
wherein coordinate ζ is the CBM data normalization.

3. The method of claim 2, wherein the CBM data normalization factor ζ is computed from scanner normalization factors Z accounting for the axial patient bed motion during the CBM acquisition according to the equation:

$$n^{-1}_{\rho\theta\zeta} = \int_0^{t_{acq}} dt \sum_z e^{-\lambda t} d_{\rho\theta z}(t) n^{-1}_{\rho\theta z} \delta_{z,Z}(\zeta, t);$$

wherein λ is decay correction constant for a specific isotope, δ is Kronecker's delta, d is dead time correction factor, and $t_{acq}$ is CBM acquisition time.

4. The method of claim 3, wherein the scanner normalization factor Z may accommodate for the mashing and rebinning of the LORs, connecting two detector scintillation crystals i and i' into projection bin according to the equation:

$$n^{-1}_{\rho\theta z}(\varepsilon) = \sum_{i,i'} \omega_{\rho\theta z,ii'} g_{ii'} \varepsilon_i \varepsilon_{i'};$$

wherein g is the geometrical component of the normalization array; and
wherein ω is the LOR contribution factor into projection data due to mashing and spanning data compression techniques and defined by the following:

$$\varphi_{j,ii'} = \begin{cases} 1/2, & \text{if } ii' \text{ contribute to sinogram bin } j \\ 0, & \text{otherwise} \end{cases}.$$

5. The method of claim 1, wherein the step (c) comprises: maximizing the following objective function $$L_A(f) = \sum_{j=\{\rho\theta\zeta\},T} (y_{jT} \ln(\bar{y}_{jT}) - \bar{y}_{jT})$$

with regard to f for the activity reconstruction;
wherein f is activity image;
wherein ordered subsets expectation maximization algorithm is applied with one iteration and 21 subsets; and
maximizing the following objective function $$L_{CE}(\varepsilon) \sum_{j=\{\rho\theta z\},T} (y_{jT} \ln(\bar{y}_{jT}) - \bar{y}_{jT})$$

with regard to ε, wherein ε is the crystal efficiency.

6. The method of claim 1, further comprising updating the crystal efficiency normalization coefficient by updating $$\varepsilon_i^{(m+1)} = \frac{-B_i + \sqrt{B_i^2 + 4A_iC_i}}{2A_i}$$

$$A_i = \sum_j \sum_{i'} \omega_{j,ii'} g_{ii'} (\bar{p}_j(f) + S_j),$$

$$B_i = \sum_j \sum_{i'} \omega_{j,ii'} (\bar{p}_j(f) + S_j)\varepsilon_{i'}^{(m)} - A_i \varepsilon_i^{(m)}$$

$$C_i = \varepsilon_i^{(m)} \sum_{jT} \frac{y_{jT}}{\bar{y}_{jT}^{(m)}(f, \varepsilon^{(m)})} \sum_{i'} \omega_{j,ii'} (\bar{p}_{jT}(f) + S_{jT})\varepsilon_{i'}^{(m)}$$

$$j = \{\rho\theta z\},$$

wherein m is iteration number for the updating the crystal efficiency ε; and
wherein $\bar{p}_j$ and $S_j$ represent summation of $\bar{p}_{jT}$ and $S_{jT}$ over TOF bin index T.

7. A positron emission tomography (PET) calibration system comprising:
a PET scanner having a patient bed that moves a patient in an axial motion through the PET scanner during the CBM acquisition; and
a scintillation crystal efficiency calibration system that performs a method comprising:
(a) generating time-of-flight (TOF) patient data of positron annihilation activity in a patient during the CBM acquisition, while accounting for the axial motion of the patient bed during the CBM acquisition, as a first data set;
(b) generating a complimentary data set by integrating the TOF patient data over the axial motion of the patient bed during the CBM acquisition, wherein the complimentary data set is modeled by the equation:

$$\bar{y}_{\rho\theta zT} = n_{\rho\theta z}^{-1}(\varepsilon)B\left(a_{\rho\theta\zeta} \sum_k C_{\rho\theta\zeta T,k} f_k\right) + n_{\rho\theta z}^{-1}(\varepsilon)B(S_{\rho\theta\zeta T}) + \bar{r}_{\rho\theta zT} =$$

$$n_{\rho\theta z}^{-1}(\varepsilon)\bar{p}_{\rho\theta zT} + n_{\rho\theta z}^{-1}(\varepsilon)S_{\rho\theta zT} + \bar{r}_{\rho\theta zT},$$

wherein $Y_{\rho\theta z}$, a motion blurring operator, is calculated by:

$$y_{\rho\theta z} = B(y_{\rho\theta\zeta}) = \int_0^{t'_{acq}} dt' \sum_\zeta e^{-\lambda t} d_{\rho\theta z}(t) y_{\rho\theta\zeta} \delta_{z,Z(\zeta,t)};$$

and
(c) simultaneously reconstructing the positron annihilation activity and crystal efficiency normalization coefficient from the complimentary data set.

8. The system of claim 7, wherein the step (a) comprises CBM data y with spatial projection index j=(ρ, θ, ζ) and TOF bin index T is modeled by combining the true events modeled projection $\bar{p}$ from the emission object f, defined by voxel index k, corrected for scanner efficiency through a normalization array n for attenuation by a, and scatter estimation S, corrected for scanner efficiency, and mean random data $\bar{r}$:

$$\bar{y}_{\rho\theta\zeta T} = a_{\rho\theta\zeta} n_{\rho\theta\zeta}^{-1}(\varepsilon) \sum_k C_{\rho\theta\zeta T,k} f_k + n_{\rho\theta\zeta}^{-1} S_{\rho\theta\zeta T} + \bar{r}_{\rho\theta\zeta T} =$$

$$a_{\rho\theta\zeta} n_{\rho\theta\zeta}^{-1}(\varepsilon) \bar{p}_{\rho\theta\zeta T} + n_{\rho\theta\zeta}^{-1} S_{\rho\theta\zeta T} + \bar{r}_{\rho\theta\zeta T};$$

wherein C is the geometrical projection system matrix;
wherein ε is the crystal efficiency; and
wherein coordinate ζ is the CBM data normalization.

9. The system of claim 8, wherein the CBM data normalization factor ζ is computed from scanner normalization factors Z accounting for the axial patient bed motion during the CBM acquisition according to the equation:

$$n_{\rho\theta\zeta}^{-1} = \int_0^{t_{acq}} dt \sum_z e^{-\lambda t} d_{\rho\theta z}(t) n_{\rho\theta z}^{-1} \delta_{z,Z(\zeta,t)};$$

wherein λ is decay correction constant for a specific isotope, δ is Kronecker's delta, d is dead time correction factor, and $t_{acq}$ is CBM acquisition time.

10. The system of claim 9, wherein the scanner normalization factor Z may accommodate for the mashing and rebinning of the LORs, connecting two detector scintillation crystals i and i' into projection bin according to the equation:

$$n_{\rho\theta z}^{-1}(\varepsilon) = \sum_{i,i'} \omega_{\rho\theta z,ii'} g_{ii'} \varepsilon_i \varepsilon_{i'};$$

wherein g is the geometrical component of the normalization array; and
wherein ω is the LOR contribution factor into projection data due to mashing and spanning data compression techniques and defined by the following:

$$\varphi_{j,ii'} = \begin{cases} 1/2, & \text{if } ii' \text{ contribute to sinogram bin } j \\ 0, & \text{otherwise} \end{cases}.$$

11. The system of claim 7, wherein the step (c) comprises: maximizing the following objective function $$L_A(f) = \sum_{j=\{\rho\theta\zeta\},T} (y_{jT} \ln(\bar{y}_{jT}) - \bar{y}_{jT})$$

with regard to f for the activity reconstruction;
wherein f is activity image;
wherein ordered subsets expectation maximization algorithm is applied with one iteration and 21 subsets; and
maximizing the following objective function $$L_{CE}(\varepsilon) \sum_{j=\{\rho\theta z\},T} (y_{jT} \ln(\bar{y}_{jT}) - \bar{y}_{jT})$$

with regard to ε, wherein ε is the crystal efficiency.

12. The system of claim 7, further comprising updating the crystal efficiency normalization coefficient by updating $$\varepsilon_i^{(m+1)} = \frac{-B_i + \sqrt{B_i^2 + 4A_iC_i}}{2A_i}$$

-continued $$A_i = \sum_j \sum_{i'} \omega_{j,ii'} g_{ii'}(\overline{p}_j(f) + S_j),$$

$$B_i = \sum_j \sum_{i'} \omega_{j,ii'}(\overline{p}_j(f) + S_j)\varepsilon_{i'}^{(m)} - A_i \varepsilon_i^{(m)}$$

$$C_i = \varepsilon_i^{(m)} \sum_{jT} \frac{y_{jT}}{\overline{y}_{jT}^{(m)}(f, \varepsilon^{(m)})} \sum_{i'} \omega_{j,ii'}(\overline{p}_{jT}(f) + S_{jT})\varepsilon_{i'}^{(m)}$$

$$j = \{\rho\theta z\},$$

wherein m is iteration number for the updating the crystal efficiency ε; and wherein $\overline{p}_j$ and $S_j$ represent summation of $\overline{p}_{jT}$ and $S_{jT}$ over TOF bin index T.

13. A non-transitory, machine readable storage medium encoded with computer program software, such that when a processor executes the computer program software, the processor performs a method for simultaneously monitoring a positron emission tomography (PET) scanner performance during a continuous-bed-motion (CBM) acquisition, wherein the PET scanner has a patient bed that moves a patient in an axial motion through the PET scanner during the CBM acquisition, the method comprising:

(a) generating time-of-flight (TOF) patient data of positron annihilation activity in a patient during the CBM acquisition, while accounting for the axial motion of the patient bed during the CBM acquisition, as a first data set;

(b) generating a complimentary data set by integrating the TOF patient data over the axial motion of the patient bed during the CBM acquisition, wherein the complimentary data set is modeled by the equation:

$$\overline{y}_{\rho\theta zT} = n_{\rho\theta z}^{-1}(\varepsilon)B\left(a_{\rho\theta\zeta}\sum_k C_{\rho\theta\zeta T,k}f_k\right) + n_{\rho\theta z}^{-1}(\varepsilon)B(S_{\rho\theta\zeta T}) + \overline{r}_{\rho\theta zT} =$$

$$n_{\rho\theta z}^{-1}(\varepsilon)\overline{p}_{\rho\theta zT} + n_{\rho\theta z}^{-1}(\varepsilon)S_{\rho\theta zT} + \overline{r}_{\rho\theta zT}$$

wherein $Y_{\rho\theta z}$, a motion blurring operator, is calculated by:

$$y_{\rho\theta z} = B(y_{\rho\theta\zeta}) = \int_0^{t'_{acq}} dt' \sum_\zeta e^{-\lambda t} d_{\rho\theta z}(t) y_{\rho\theta\zeta} \delta_{z,Z(\zeta,t)};$$

and (c) simultaneously reconstructing the positron annihilation activity and crystal efficiency normalization coefficient from the complimentary data set.

14. The non-transitory, machine readable storage medium of claim 13, wherein the step (a) comprises CBM data y with spatial projection index j =(ρ, θ, ζ) and TOF bin index T is modeled by combining the true events modeled projection $\overline{p}$ from the emission object f, defined by voxel index k, corrected for scanner efficiency through a normalization array n for attenuation by a, and scatter estimation S, corrected for scanner efficiency, and mean random data $\overline{r}$:

$$\overline{y}_{\rho\theta\zeta T} = a_{\rho\theta\zeta}n_{\rho\theta\zeta}^{-1}(\varepsilon)\sum_k C_{\rho\theta\zeta T,k}f_k + n_{\rho\theta\zeta}^{-1}S_{\rho\theta\zeta T} + \overline{r}_{\rho\theta\zeta T} =$$

$$a_{\rho\theta\zeta}n_{\rho\theta\zeta}^{-1}(\varepsilon)\overline{p}_{\rho\theta\zeta T} + n_{\rho\theta\zeta}^{-1}S_{\rho\theta\zeta T} + \overline{r}_{\rho\theta\zeta T};$$

wherein C is the geometrical projection system matrix;
wherein ε is the crystal efficiency; and
wherein coordinate ζ is the CBM data normalization.

15. The non-transitory, machine readable storage medium of claim 13, wherein the CBM data normalization factor ζ is computed from scanner normalization factors Z accounting for the axial patient bed motion during the CBM acquisition according to the equation:

$$n_{\rho\theta\zeta}^{-1} = \int_0^{t_{acq}} dt \sum_z e^{-\lambda t} d_{\rho\theta z}(t) n_{\rho\theta z}^{-1} \delta_{z,Z(\zeta,t)};$$

wherein λ is decay correction constant for a specific isotope, δ is Kronecker's delta, d is dead time correction factor, and $t_{acq}$ is CBM acquisition time.

16. The non-transitory, machine readable storage medium of claim 13, wherein the scanner normalization factor Z may accommodate for the mashing and rebinning of the LORs, connecting two detector scintillation crystals i and i' into projection bin according to the equation:

$$n_{\rho\theta z}^{-1}(\varepsilon) = \sum_{i,i'} \omega_{\rho\theta z,ii'} g_{ii'} \varepsilon_i \varepsilon_{i'};$$

wherein g is the geometrical component of the normalization array; and
wherein ω is the LOR contribution factor into projection data due to mashing and spanning data compression techniques and defined by the following:

$$\omega_{j,ii'} = \begin{cases} 1/2, & \text{if } ii' \text{ contribute to sinogram bin } j \\ 0, & \text{otherwise} \end{cases}.$$

17. The non-transitory, machine readable storage medium of claim 13, wherein the step (c) comprises:
maximizing the following objective function $$L_A(f) = \sum_{j=\{\rho\theta\zeta\},T} (y_{jT}\ln(\overline{y}_{jT}) - \overline{y}_{jT})$$

with regard to f for the activity reconstruction;
wherein f is activity image;
wherein ordered subsets expectation maximization algorithm is applied with one iteration and 21 subsets; and
maximizing the following objective function $$L_{CE}(\varepsilon) = \sum_{j=\{\rho\theta\zeta\},T} (y_{jT}\ln(\overline{y}_{jT}) - \overline{y}_{jT})$$

with regard to ε, wherein ε is the crystal efficiency.

18. The non-transitory, machine readable storage medium of claim 13, further comprising updating the crystal efficiency normalization coefficient by updating $$\varepsilon_i^{(m+1)} = \frac{-B_i + \sqrt{B_i^2 + 4A_iC_i}}{2A_i}$$

$$A_i = \sum_j \sum_{i'} \omega_{j,ii'} g_{ii'} (\bar{p}_j(f) + S_j),$$

$$B_i = \sum_j \sum_{i'} \omega_{j,ii'} (\bar{p}_j(f) + S_j)\varepsilon_{i'}^{(m)} - A_i \varepsilon_i^{(m)}$$

$$C_i = \varepsilon_i^{(m)} \sum_{jT} \frac{y_{jT}}{\bar{y}_{jT}^{(m)}(f, \varepsilon^{(m)})} \sum_{i'} \omega_{j,ii'} (\bar{p}_{jT}(f) + S_{jT})\varepsilon_{i'}^{(m)}$$

$$j = \{\rho\theta z\},$$

wherein m is iteration number for the updating the crystal efficiency $\varepsilon$; and wherein $\bar{p}_j$ and $S_j$ represent summation of $\bar{p}_{jT}$ and $S_{jT}$ over TOF bin index T.

* * * * *